(12) United States Patent
Rasekhi

(10) Patent No.: US 7,588,202 B2
(45) Date of Patent: Sep. 15, 2009

(54) APPARATUS FOR MILLING MATERIAL

(76) Inventor: Houshang Rasekhi, 2100 Debeers Dr., Sandy, UT (US) 84093

( * ) Notice: Subject to any disclaimer, the term of this patent is extended or adjusted under 35 U.S.C. 154(b) by 285 days.

(21) Appl. No.: 11/623,623

(22) Filed: Jan. 16, 2007

(65) Prior Publication Data

US 2007/0164137 A1      Jul. 19, 2007

Related U.S. Application Data

(60) Provisional application No. 60/812,867, filed on Jun. 12, 2006, provisional application No. 60/759,475, filed on Jan. 17, 2006.

(51) Int. Cl.
  *B02C 18/16*    (2006.01)
(52) U.S. Cl. .................. 241/92; 241/100; 241/224; 241/262; 241/606
(58) Field of Classification Search .............. 241/92, 241/94, 606, 46.06, 169.1, 243, 261, 100, 241/262, 224
See application file for complete search history.

(56) References Cited

U.S. PATENT DOCUMENTS

| | | | | |
|---|---|---|---|---|
| 2,583,595 | A | * | 1/1952 | Albert et al. ............... 83/145 |
| 2,761,627 | A | * | 9/1956 | Reed ..................... 241/46.013 |
| 3,528,617 | A | * | 9/1970 | Trevathan ................. 241/92 |
| 4,101,082 | A | | 7/1978 | Mayer et al. |
| 4,216,919 | A | * | 8/1980 | Trevathan ................. 241/92 |
| 4,252,282 | A | | 2/1981 | Vermeulen et al. |
| 4,469,283 | A | | 9/1984 | Noguchi et al. |
| 5,048,764 | A | | 9/1991 | Flament |
| 5,062,576 | A | | 11/1991 | Burda |
| 5,201,475 | A | | 4/1993 | Nakagomi |
| 5,487,509 | A | | 1/1996 | Hama |
| 5,683,406 | A | | 11/1997 | Altobelli et al. |
| 5,769,853 | A | | 6/1998 | Quétin |
| 5,810,472 | A | | 9/1998 | Penaranda et al. |
| 5,817,097 | A | | 10/1998 | Howard et al. |
| 5,906,322 | A | | 5/1999 | Hama |
| 5,918,821 | A | | 7/1999 | Grooms et al. |
| 6,109,551 | A | * | 8/2000 | Sullivan ................. 241/46.013 |
| 6,287,312 | B1 | | 9/2001 | Clokie et al. |
| 6,318,651 | B1 | | 11/2001 | Spiering |
| 6,402,070 | B1 | | 6/2002 | Ishida et al. |
| 6,484,954 | B2 | | 11/2002 | Lenox |
| 6,755,365 | B1 | | 6/2004 | Meredith |
| RE38,630 | E | | 10/2004 | Lazzara et al. |
| 6,824,087 | B2 | | 11/2004 | McPherson et al. |
| 7,137,581 | B2 | | 11/2006 | Takayama et al. |
| 2002/0040943 | A1 | | 4/2002 | Lenox |
| 2005/0173573 | A1 | | 8/2005 | Hay et al. |
| 2005/0194481 | A1 | | 9/2005 | Hay et al. |
| 2006/0138260 | A1 | | 6/2006 | Hay et al. |

* cited by examiner

*Primary Examiner*—Mark Rosenbaum
(74) *Attorney, Agent, or Firm*—Austin Rapp & Hardman

(57) ABSTRACT

An apparatus for milling material is disclosed. The apparatus may include a base surface. The base surface may include a first cutting tooth for milling the material. The base surface may include a first aperture of a predetermined diameter. The first aperture may be disposed adjacent the first cutting tooth so that material of less than the predetermined diameter may pass through the first aperture. The apparatus may include a trimming member. The trimming member may include a first rib for interfacing with the first cutting tooth to facilitate the milling of the material. The base surface and the trimming member may move relative to each other. The base surface and the trimming member may interface to mill material placed on the base surface.

31 Claims, 12 Drawing Sheets

APPARATUS FOR MILLING MATERIAL

RELATED APPLICATIONS

This application is related to and claims priority from Provisional U.S. Patent Application Ser. No. 60/759,475 filed Jan. 17, 2006, for a New and Improved Bone Mill with Vacuum Mixing System, with inventor Houshang Rasekhi and Provisional U.S. Patent Application Ser. No. 60/812,867 filed Jun. 12, 2006, for a New and Improved Bone Mill with Reciprocating Self-Clearing Rasp and Vacuum Mixing System, with inventor Houshang Rasekhi which are both incorporated herein by reference. The present specification focuses on general elements of the present invention. By doing so, Applicant does not intend to limit the scope of the present invention.

TECHNICAL FIELD

The present invention relates generally to milling devices. More specifically, the present invention relates to an apparatus for milling material, particularly bone material.

BACKGROUND

Bone grafting is often used in orthopedic procedures to either stimulate bone to heal or provide support to the skeleton. Bone grafts are bones that are transplanted from one area of the skeleton to another. Bone or bone-like materials in bone grafts may come from the patient (autograft bone), from a donor (allograft bone) or from a man-made source (alloplast bone). In many cases the bone grafts may be used to fill in a space created by disease, injury, deformity, or surgical procedure such as spinal fusion.

The autograft bones (chips) may be harvested from the bones of the hip, the ribs or legs during the same operating procedures. Subsequently the harvested bone chips may be cut into smaller pieces creating bone powder. The autograft bone powder may be mixed with selected fluids to create a bone paste.

The available bone mills generally suffer from either inability to reproduce bone powder with predictable bone particle size distribution or damage the bone particles by transferring degrading heat to the bone particles.

These problems may also arise in other milling contexts. Accordingly, a need may exist for an apparatus for milling material that may create milled material with a predictable particle size distribution without damaging the material by transferring degrading heat to the milled material.

SUMMARY OF THE INVENTION

An apparatus for milling material to a predetermined particle size distribution profile is disclosed. The apparatus includes a base surface. The base surface includes a first cutting tooth for milling the material. The base surface also includes a first aperture of a predetermined diameter disposed adjacent the first cutting tooth so that material of less than the predetermined diameter may pass through the first aperture. The apparatus also includes a trimming member. The trimming member includes a first rib for interfacing with the first cutting tooth to facilitate the milling of the material. The base surface and the trimming member move relative to each other and interface to mill material placed on the base surface.

In some embodiments, the base surface includes a second cutting tooth. In further embodiments, the trimming member includes a second rib that interfaces with the second cutting tooth to facilitate the milling of the material.

The first cutting tooth and the second cutting tooth, in some embodiments, are different sizes such that the material is milled to fit a predetermined particle size distribution profile. In other embodiments, the first cutting tooth and the second cutting tooth are offset from each other.

In some embodiments, the first cutting tooth and the second cutting tooth are offset from each other in the radial direction. In other embodiments, the first cutting tooth and the second cutting tooth are offset from each other in the circumferential direction. In further embodiments, the first cutting tooth and the second cutting tooth are offset from each other in the lateral direction. In still further embodiments, the first cutting tooth and the second cutting tooth are offset from each other in the longitudinal direction. In some embodiments, the first cutting tooth and the second cutting tooth are offset from each other in multiple directions.

The first cutting tooth, in some embodiments, includes a first inclined face. In further embodiments, the first aperture is arcuately aligned with the first inclined face. In still further embodiments, the first aperture is disposed adjacent the first inclined face and an angle between the first inclined face and the base surface is less than about ninety degrees. In some embodiments, the base surface includes a second aperture of a predetermined diameter so that material of less than the predetermined diameter may pass through the second aperture. In other embodiments, the first cutting tooth includes a second inclined face, the base surface includes a third aperture of a predetermined diameter disposed adjacent the first cutting tooth so that material of less than the predetermined diameter may pass through the third aperture, and the third aperture is disposed adjacent the second inclined face.

In some embodiments, at least one of the first aperture, the second aperture, and the third aperture have a different size such that the material is milled to fit a predetermined particle size distribution profile. In other embodiments, the apparatus includes a push surface disposed to direct the material toward the base surface and to restrict movement of the material on the base surface. In further embodiments, the apparatus includes a container for collecting material passing through the apertures during milling. In still further embodiments, the apparatus includes a drive mechanism for moving the base surface and trimming member relative to each other.

Another embodiment of an apparatus for milling material to within a predetermined particle size distribution profile is described. The apparatus includes a base surface. The base surface includes a first cutting tooth for milling the material. The base surface also includes a first aperture of a predetermined diameter disposed adjacent the first cutting tooth so that material of less than the predetermined diameter may pass through the first aperture. The apparatus includes a trimming member. The trimming member includes a first rib for interfacing with the first cutting tooth to facilitate the milling of the material. The base surface and the trimming member move longitudinally relative to each other and interface to mill material placed on the base surface.

In some embodiments, the base surface includes a second cutting tooth and the trimming member includes a second rib that interfaces with the second cutting tooth to facilitate the milling of the material. In further embodiments, the first cutting tooth and the second cutting tooth are offset from each other. In other embodiments, the first cutting tooth and the second cutting tooth are laterally and/or longitudinally offset from each other.

The apparatus, in some embodiments, includes a push surface disposed to direct the material toward the base surface and to restrict vertical movement of the material on the base surface. In further embodiments, the push surface is connected to a push rod disposed to direct the material toward the base surface and to restrict movement of the material on the base surface.

In some embodiments, the apparatus includes a drive mechanism for moving the base surface and trimming member relative to each other. In further embodiments, the apparatus includes a container for collecting material passing through the apertures during milling. In still further embodiments, the container for collecting material passing through the apertures during milling may be used to dispense the material.

A further embodiment of an apparatus for milling material to within a predetermined particle size distribution profile is described. The apparatus includes a base surface. The base surface includes a first cutting tooth for milling the material. The base surface also includes a first aperture of a predetermined diameter disposed adjacent the first cutting tooth so that material of less than the predetermined diameter may pass through the first aperture. The apparatus includes a trimming member. The trimming member includes a first rib for interfacing with the first cutting tooth to facilitate the milling of the material. The base surface and the trimming member move radially relative to each other and interface to mill material placed on the base surface.

In some embodiments, the base surface includes a second cutting tooth and the trimming member includes a second rib that interfaces with the second cutting tooth to facilitate the milling of the material. In further embodiments, the first cutting tooth and the second cutting tooth are offset from each other. In still further embodiments, the first cutting tooth and the second cutting tooth are radially and/or circumferentially offset from each other.

The apparatus, in some embodiments, includes a push surface disposed to direct the material toward the base surface. In further embodiments, the push surface includes a wedge disposed to direct the material toward the base surface as the material is moved by centrifugal motion in the radial direction.

In some embodiments, the apparatus includes a spider construct that encourages the material away from the axis of rotation so that centrifugal force will act upon the material as the apparatus is rotated. In further embodiments, the apparatus includes a rotatable mixer paddle that is connected to the trimming member such that the rotatable mixer paddle moves relative to the base surface. In still further embodiments, the apparatus includes a drive mechanism for moving the base surface and trimming member relative to each other and for rotating the mixer paddle to mix the material. In still further embodiments, the apparatus includes a container for collecting material passing through the apertures during milling.

BRIEF DESCRIPTION OF THE DRAWINGS

Exemplary embodiments of the invention will become more fully apparent from the following description and appended claims, taken in conjunction with the accompanying drawings. Understanding that these drawings depict only exemplary embodiments and are, therefore, not to be considered limiting of the invention's scope, the exemplary embodiments of the invention will be described with additional specificity and detail through use of the accompanying drawings in which:

DETAILED DESCRIPTION

Various embodiments of the invention are now described with reference to the Figures, where like reference numbers indicate identical or functionally similar elements. The embodiments of the present invention, as generally described and illustrated in the Figures herein, could be arranged and designed in a wide variety of different configurations. Thus, the following more detailed description of several exemplary embodiments of the present invention, as represented in the Figures, is not intended to limit the scope of the invention, as claimed, but is merely representative of the embodiments of the invention.

The word "exemplary" is used exclusively herein to mean "serving as an example, instance, or illustration." Any embodiment described herein as "exemplary" is not necessarily to be construed as preferred or advantageous over other embodiments.

As used herein, the terms "an embodiment," "embodiment," "embodiments," "the embodiment," "the embodiments," "one or more embodiments," "some embodiments," "certain embodiments," "one embodiment," "another embodiment" and the like mean "one or more (but not necessarily all) embodiments of the disclosed invention(s)," unless expressly specified otherwise.

The phrase "based on" does not mean "based only on," unless expressly specified otherwise. In other words, the phrase "based on" describes both "based only on" and "based at least on."

Figure 1:
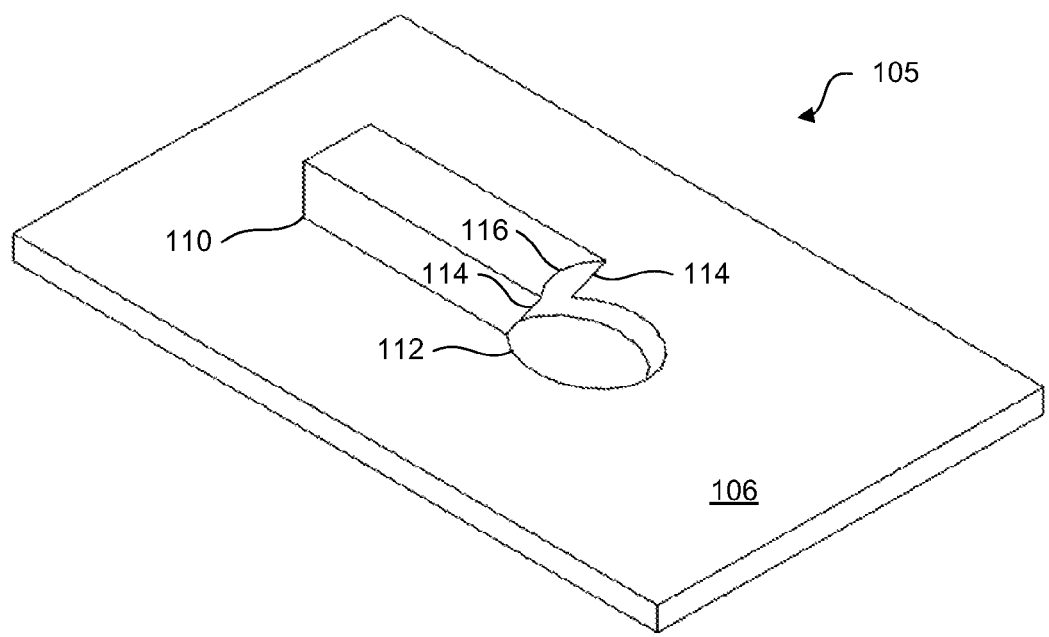
FIG. 1 is a perspective cut away of an embodiment of a rasp for milling material.
Figure 2:
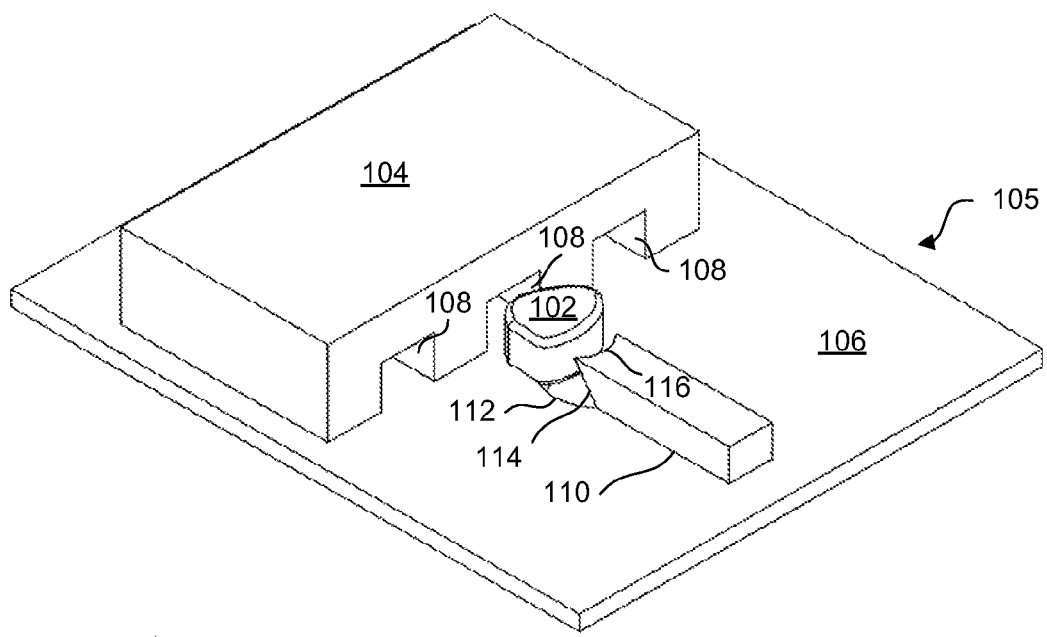
FIG. 2 is a perspective cut away of an embodiment of a rasp and trimming member for milling material.

FIG. 1 is a perspective cut away of an embodiment of a rasp 105 for milling material 102. FIG. 2 is a perspective cut away of an embodiment of a rasp 105 and trimming member 104 for milling material 102. The rasp 105 may include a base surface 106. The trimming member 104 may include ribs 108. The base surface 106 includes a cutting tooth 110 and an aperture 112. The cutting tooth 110 may protrude from the base surface 106. The cutting tooth 110 may include an inclined face 114. The inclined face 114 of the cutting tooth 110 may terminate in a cutting edge 116.

The rasp 105 and the trimming member 104 may move relative to each other. For example, the rasp 105 may move with respect to the trimming member 104, the trimming member 104 may move with respect to the rasp 105, and/or the rasp 105 and the trimming member 104 may move with respect to each other. The rasp 105 and the trimming member 104 may move radially, longitudinally, or in any other direction that may allow the rasp 105 and the trimming member 104 to interface to mill material 102 placed on the base surface 106.

The rasp 105 and the trimming member 104 may interface to mill material 102 placed on the base surface 106. For example, the cutting tooth 110 may pass near a rib 108 when the rasp 105 and the trimming member 104 move with respect to each other. In the present embodiment, the cutting tooth 110 may pass near two ribs 108 when the base surface 106 and the trimming member 104 move with respect to each other.

The aperture 112 may be arcuately aligned with the inclined face 114 of the cutting tooth 110. For the purpose of this disclosure, arcuately aligned may include aligning a portion of the inclined face 114 with a portion of the aperture 112. For example, the aperture 112 and the inclined face 114 may be formed by drilling into the rasp 105. A drill may enter the rasp 105 at an angle that is not perpendicular to the base surface 106, such that an axis of the inclined face 114 and an axis of the aperture 112 may be at an angle from the base surface 106 of less than approximately ninety degrees. This may facilitate the sieving action of the milled material 102 as will be explained further below.

The cutting tooth 110 may engage a piece of the material 102 to be milled. For example, the cutting tooth 110 may push the material 102 toward the trimming member 104. The material 102 may abut the trimming member 104. The cutting tooth 110 may remove a portion of the material 102 when the material 102 abuts the trimming member 104 and the cutting tooth 110. In this manner, material 102 may be cut rather than crushed, which may heat and potentially damage the material 102.

The aperture 112 and the inclined face 114 may cooperate to direct the removed portion of the material 102 through the aperture 112 below the base surface 106. For example, as the cutting tooth 110 removes a portion of the material 102, the removed portion of the material 102 may abut the inclined face 114 and a portion of the aperture 112 such that the removed portion of the material 102 may be pushed below the base surface 106. In this manner, the base surface 106 and the aperture 112 act much like a sieve to allow only material of a desired size or smaller to pass through the base surface 106. In other embodiments, the base surface 106 may not be located below the material 102 such that removed portions of the material 102 may pass through the apertures 112 with the aid of gravity, but rather may be located above the material 102 such that removed portions of the material 102 may pass through the apertures 112 with the aid of another force, such as a force created by the angle of the inclined face 114 and/or other force.

The size of the aperture 112 and/or the angle of the inclined face 114 may be selected to achieve a predetermined particle size distribution profile. The cutting tooth 110 may remove portions of the material 102 that are approximately the size of the aperture 112, smaller than the size of the aperture 112, and/or larger than the size of the aperture 112. When a removed portion of the material 102 is larger than the size of the aperture 112, the cutting tooth 110 may push the removed portion of the material 102 into the trimming member 104 and remove another portion of the material 102. This process may be repeated until all of the material 102 to be milled has been directed through the aperture 112.

Particle size distribution profiles may include the varying sizes of the milled material 102. The particle size distribution profile may represent a bell shaped curve of the various particle sizes. In some embodiments, after milling the material 102, the particle size distribution profile may include a small range of particle sizes. A particle size distribution profile with a small range of particle sizes may be advantageous in applications requiring specific profiles.

The rasp 105 may include apertures 112 of varying diameters and/or cutting teeth 110 of varying sizes. For example, one aperture 112 may have a first predetermined diameter and/or cutting tooth 110 size, a second aperture 112 may have a second predetermined diameter and/or cutting tooth 110 size, and a third aperture 112 may have a third predetermined diameter and/or cutting tooth 110 size. Varying the diameters, or sizes, of the apertures 112 and/or cutting teeth 110 may facilitate achieving desired particle size distribution profiles.

Figure 3:
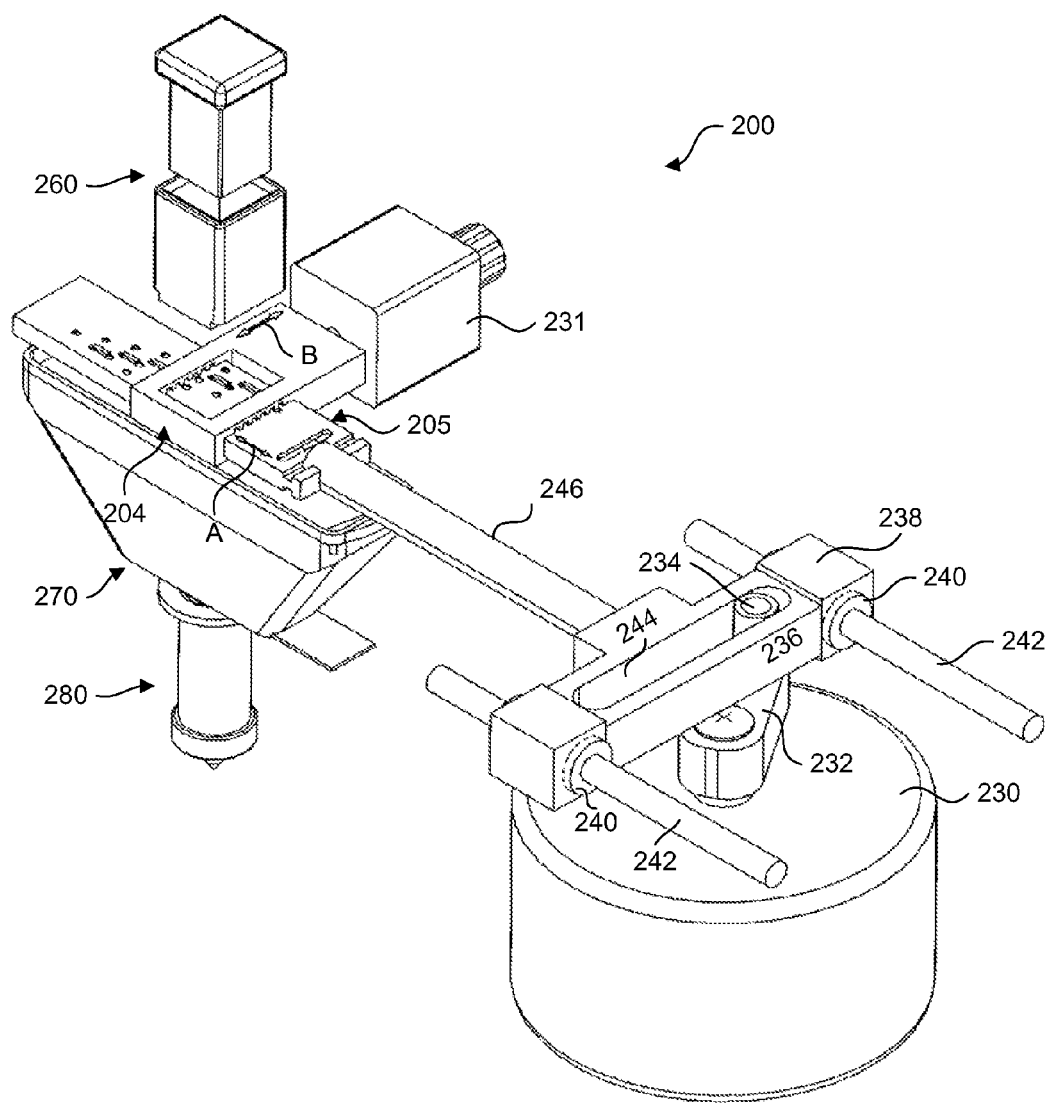
FIG. 3 is a perspective view of a longitudinal embodiment of an apparatus for milling material.

FIG. 3 is a perspective view of a longitudinal embodiment of an apparatus 200 for milling material 102. The apparatus 200 may include a rasp 205 and a trimming member 204.

The apparatus 200 may include a hopper assembly 260, a collector assembly 270, and/or a dispenser 280. These elements will be discussed in more detail in connection with FIGS. 5-7.

The present embodiment is a longitudinal embodiment of an apparatus 200 for milling material 102, because the rasp 205 and the trimming member 204 may move longitudinally relative to each other. The rasp 205 may be moved relative to the trimming member 204 by a driving mechanism. A driving mechanism may include any mechanism that may move the rasp 205 and/or the trimming member 204 with respect to each other. For example, a driving mechanism may include a user that may move the rasp 205 and/or the trimming member 204 with respect to each other. In another example, a driving mechanism may include a motor that may move the rasp 205 and/or the trimming member 204 with respect to each other. In the present embodiment, the driving mechanism may include a rotary motor 230 and a linear motor 231.

The rotary motor 230 may rotate a cam 232. The cam 232 may include a pin 234, which may be connected to a bearing 236. The cam 232 may move a sliding mechanism 238. The sliding mechanism 238 may include linear bearings 240. The linear bearings 240 may slide on two bars 242. The pin 234 of the cam 232 with its bearing 236 may be contained within a slot 244. The pin 234 may drive the sliding mechanism 238 such that the sliding mechanism 238 generates reciprocating linear motion. The sliding mechanism 238 may be connected to a member 246. The member 246 may translate the force from the sliding mechanism 238 to the rasp 205, such that the rasp 205 moves reciprocally in a longitudinal direction (as shown by arrow A) relative to the trimming member 204.

The linear motor 231 may move both the rasp 205 and the trimming member 204 in a lateral direction (as shown by arrow B). This motion will be discussed in more detail in connection with FIG. 5.

Figure 4:
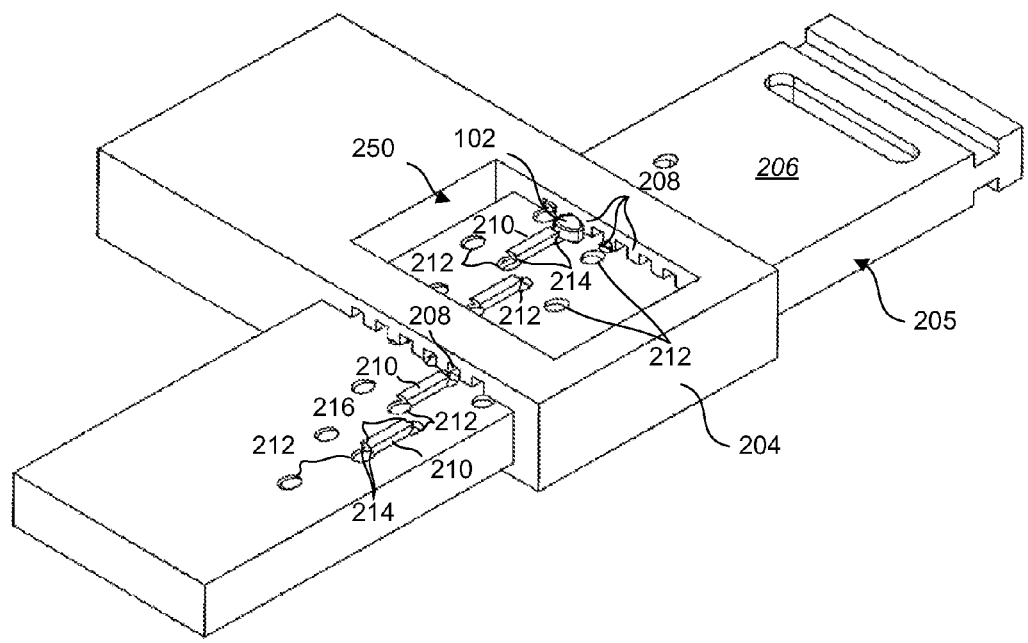
FIG. 4 is a perspective view of the rasp and trimming member of the longitudinal embodiment of the apparatus for milling material shown in FIG. 3.

FIG. 4 is a perspective view of the rasp 205 and trimming member 204 of the longitudinal embodiment of the apparatus 200 for milling material 102 shown in FIG. 3. The base surface 206 may include multiple cutting teeth 210. The cutting teeth 210, in the present embodiment, may be laterally offset from each other. For example, the cutting teeth 210 may be offset from each other in a direction perpendicular to the direction of the relative motion between the rasp 205 and the trimming member 204. The cutting teeth 210 may be longitudinally offset from each other. For example, the cutting teeth 210 may be offset from each other in the direction of the relative motion between the rasp 205 and the trimming member 204.

In the present embodiment, the cutting teeth 210 are both laterally and longitudinally offset from each other, such that no cutting tooth 210 is aligned longitudinally or laterally with another tooth 210. The trimming member 204 may include multiple ribs 208 that may interface with the various cutting teeth 210. The trimming member 204 may include an opening 250. The opening 250 may generally enclose the material 102 to be milled. In the present embodiment, the opening 250 may cut through a portion of the trimming member 204 that includes the ribs 208 such that one portion of the ribs 208 is separated from another portion of the ribs 208.

The base surface 206 may include multiple apertures 212. In the present embodiment, two apertures 212 may be disposed adjacent a cutting tooth 210. For example, the one aperture 212 may be positioned near one inclined face 214 of a cutting tooth 210 and another aperture 212 may be positioned near the other inclined face 214 of the cutting tooth 210. The base surface 206 may include other apertures 212 that may not necessarily be disposed adjacent a cutting tooth 210.

The size of the various apertures 212 and/or the angle of the inclined faces 214 may be selected to achieve a pre-determined particle size distribution profile. For example, some cutting teeth 210 may be different sizes than other cutting teeth 210 and/or some apertures 212 may be different sizes than other apertures 212. In another example, some cutting teeth 210 may include inclined faces 214 of different shapes than other inclined faces 214 and/or some apertures 212 may be of different shapes than other apertures 212.

The cutting tooth 210 may remove portions of the material 102. The removed portions of the material 102 may be of varying sizes. For example, portions of the material 102 may be removed that are approximately the size of the aperture 212, smaller than the size of the aperture 212, and/or larger than the size of the aperture 212. When a removed portion of the material 102 is larger than the size of the aperture 212, a cutting tooth 210, i.e. the same or a different cutting tooth 210, may push the removed portion of the material 102 into the trimming member 204 and remove another portion of the material 102. This process may be repeated until all of the material 102 to be milled has been directed through the aperture 212. Thus, the material 102 may be cut to generally match a predetermined varied particle size distribution profile.

The present embodiment is a longitudinal embodiment of an apparatus 200 for milling material 102, because the rasp 205 and the trimming member 204 may move longitudinally relative to each other. For example, the rasp 205 may be moved using the rotary motor 230 shown in the previous embodiment (shown in FIG. 3).

The rasp 205 may move reciprocally in a longitudinal direction relative to the trimming member 204. In embodiments where the base surface 206 may include a cutting tooth 210 with more than one cutting edge 216 and inclined face 214, this reciprocal motion may allow the cutting tooth 210 to remove portions of the material 102 to be milled on both the forward and the backward stroke of the rasp 205. For example, if the rasp 205 moves reciprocally, a cutting tooth 210 may remove portions of the material 102 to be milled as the rasp 205 and/or the trimming member 204 moves away from a driving mechanism (i.e. the forward stroke) and the cutting tooth 210 may remove portions of the material 102 to be milled as the rasp 205 and/or the trimming member 204 moves toward the driving mechanism (i.e. the backward stroke).

Figure 5:
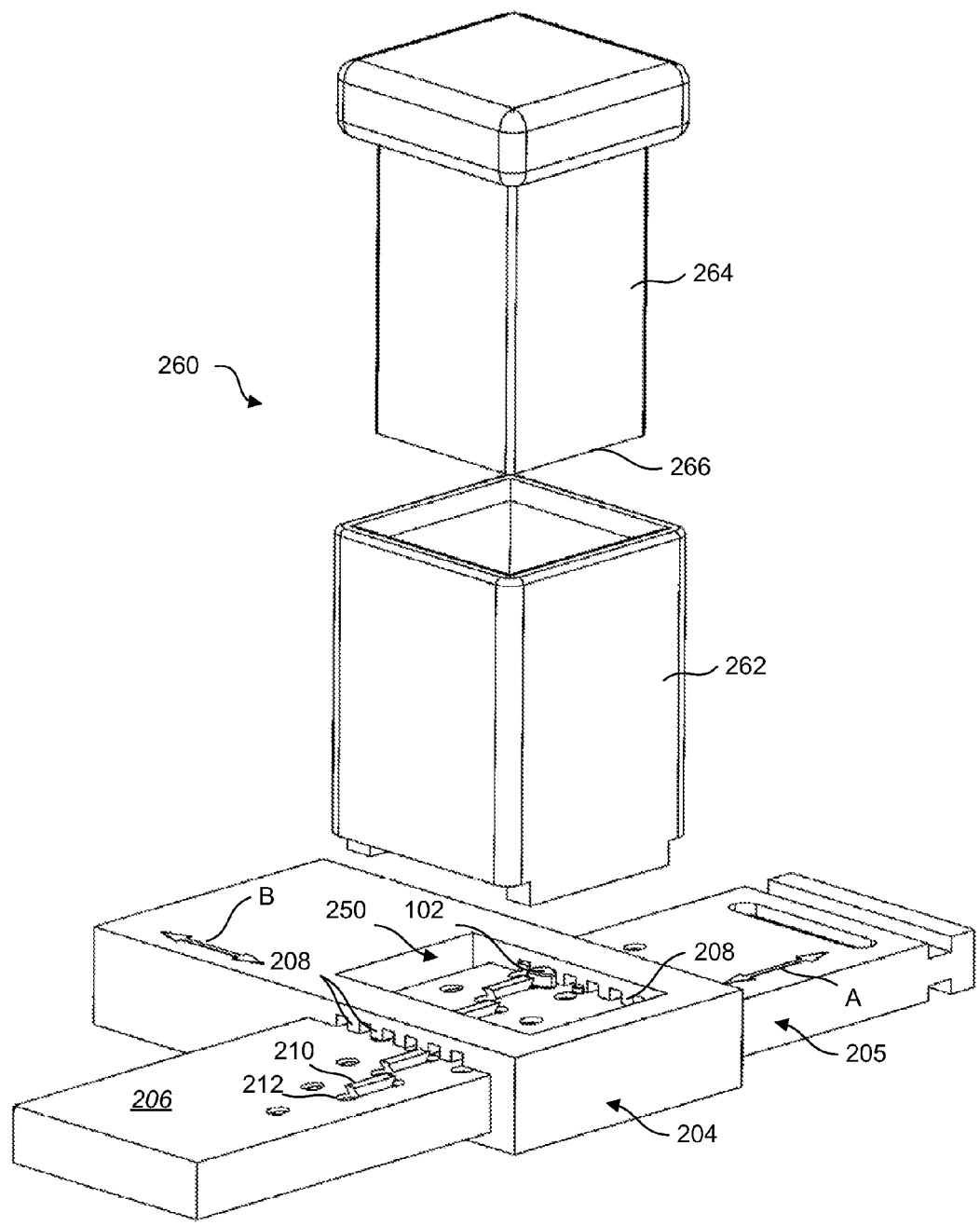
FIG. 5 is a perspective partially exploded view of a hopper assembly used in conjunction with the longitudinal embodiment of an apparatus for milling material shown in FIG. 3.

FIG. 5 is a perspective partially exploded view of a hopper assembly 260 used in conjunction with the longitudinal embodiment of an apparatus 200 for milling material 102 shown in FIG. 3. The hopper assembly 260 may include a stationary chute 262 and a push rod 264. The base surface 206 of the rasp 205 may include multiple cutting teeth 210 and apertures 212, as in the previous embodiments.

The trimming member 204 may include multiple ribs 208. The trimming member 204 may include an opening 250. The opening 250 may generally enclose the material 102 to be milled. The opening 250 may be disposed to receive the stationary chute 262 and/or push rod 264. The opening 250 may be disposed to receive the stationary chute 262 such that the stationary chute 262 may be partially inserted into the opening 250. The stationary chute 262 may also generally enclose the material 102 to be milled. The stationary chute 262 may allow the apparatus 200 to mill more material 102 by providing a temporary container for material 102 to be milled as the apparatus mills the material 102 that is within the opening 250 of the trimming member 204. For example, the stationary chute 262 may act like a hopper or the like.

The push rod 264 may be used to apply pressure to the material 102 to be milled such that it may be pressed against the base surface 206. The push rod 264 may include a push surface 266. The push surface 266 may interface with the material 102 to be milled. The push rod 264 may prevent material 102 from merely being chipped by a cutting tooth 210 by generally restraining the vertical motion of the material. For example, a piece of material 102 may be pressed against the base surface 206 by both the push rod 264 and the force of gravity such that as the cutting tooth 210 pushes the piece of material 102 against the trimming member 204, the cutting tooth 210 may remove a portion of the material 102.

During the cutting process, the material 102 to be milled and the stationary chute 262 may remain stationary. The rasp 205 may move in the longitudinal direction (as shown by arrow A) allowing the cutting teeth 210 to remove portions of the material 102. The rasp 205 and trimming member 204 may also move in the lateral direction (as shown by arrow B) such that a cutting tooth 210 that has previously cut a portion of the material 102 and/or another cutting tooth 210 may, by moving in the lateral direction with respect to the stationary material 102, cut a different portion of the material 102. This may prevent the material 102 to be milled from simply being recut by the various cutting teeth 210 with which it may come in contact.

For example, if the material 102 stays in the same position within the opening 250, i.e. the material 102 does not move in either the longitudinal or the lateral direction, a cutting tooth 210 may cut a portion of the material 102 on the first stroke of the rasp 205 leaving a groove in the material 102. On the second stroke, the cutting tooth 210 may pass through the cut groove and may remove a minimal amount of material 102 on the second and subsequent strokes. In the present embodiment, the trimming member 204 and rasp 205 may move approximately the width of one cutting tooth 210 on each stroke in the lateral direction with respect to the stationary chute 262 and the material 102 to be milled.

Figure 6:
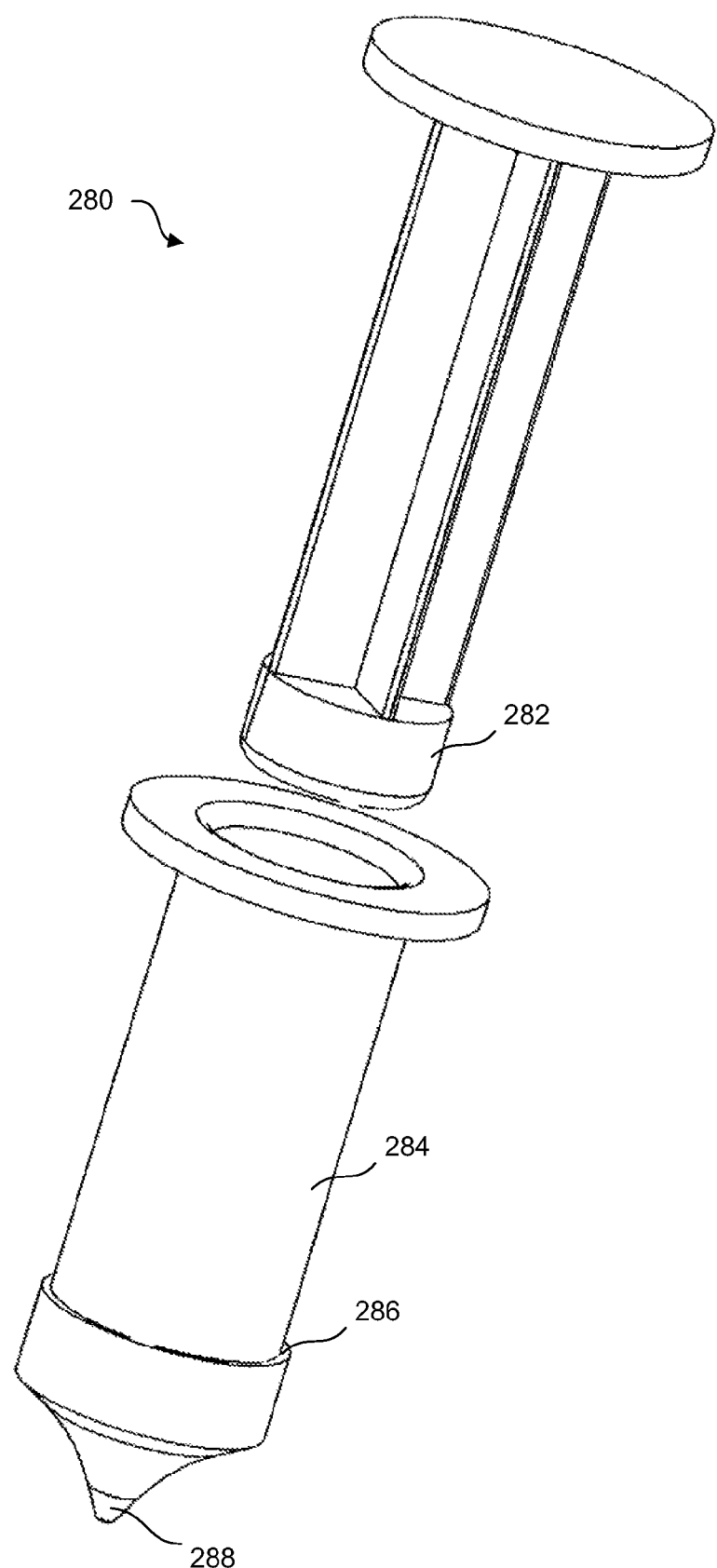
FIG. 6 is a perspective exploded view of a dispenser.

FIG. 6 is a perspective exploded view of an embodiment of a dispenser 280. The dispenser 280 may include a plunger 282. The dispenser 280 may include a boot 284. The boot 284 may include a tip 286. The tip 286 may include a hole 288 that may enlarge to facilitate dispensing of the milled material 102. For example, the dispenser 280 may contain some of the milled material 102. The plunger 282 may apply pressure to the milled material 102, which in turn may apply pressure to the tip 286 of the dispenser. As the plunger 282 applies pressure to the milled material 102, the milled material 102 may enlarge the hole 288 in the tip 286 of the dispenser 280 to allow the milled material 102 to pass therethrough.

The dispenser 280 may be used to combine the milled material 102 with other ingredients to make a bone paste. When a larger amount of bone paste is needed for larger segmental replacements in a surgical procedure a composite mixture may be used. For example, a composite mixture of calcium phosphate and collagen mixed with bone marrow and the milled material 102 may be used to fuse lumbar vertebrae. The dispenser 280 may also be used to dispense the bone paste.

Figure 7:
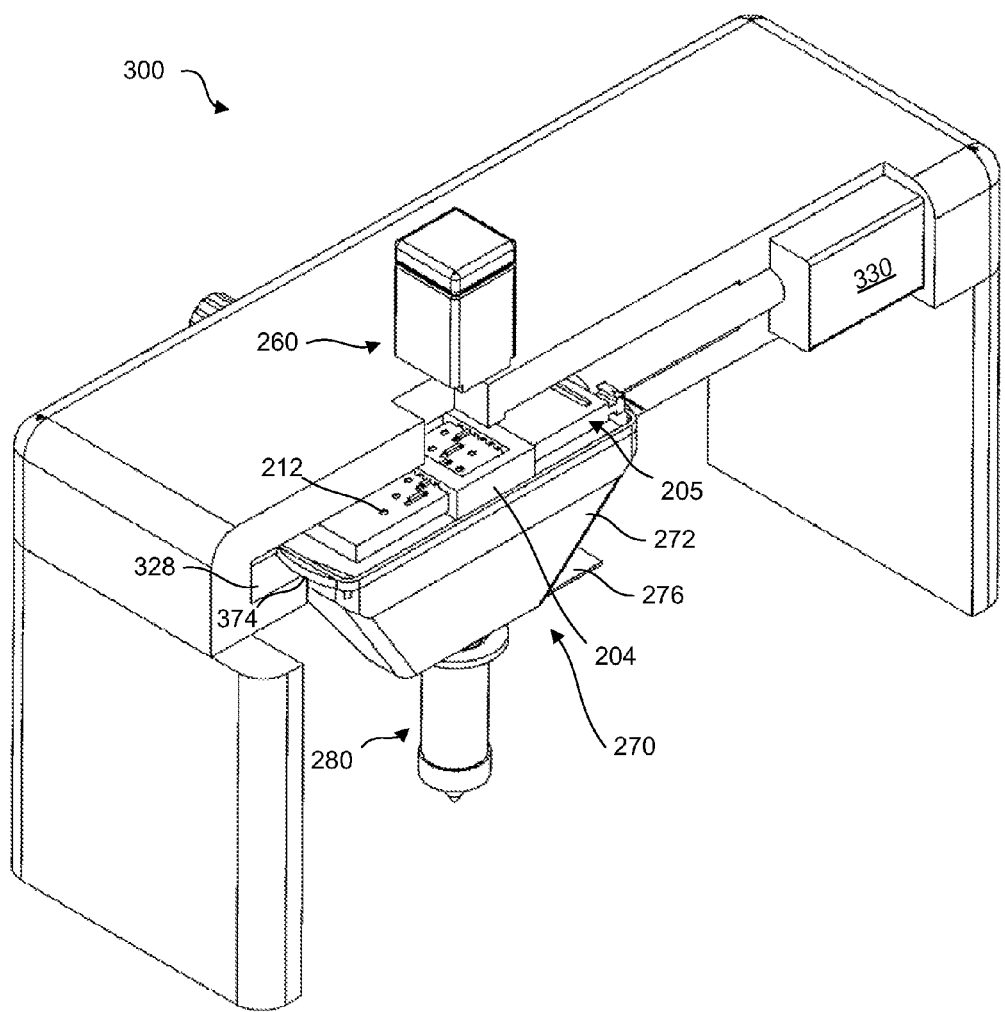
FIG. 7 is a perspective partially exploded sectional view of another longitudinal embodiment of an apparatus for milling material including a collector assembly for receiving the milled material.

FIG. 7 is a perspective partially exploded sectional view of another longitudinal embodiment of an apparatus 300 for milling material 102 including a collector assembly 270 for receiving the milled material 102. The apparatus 300 may include a linear motor 330 rather than the rotary motor 230 used in the previous embodiment (shown in FIG. 3). The apparatus 300 may include a hopper assembly 260.

The collector assembly 270 may include a container 272. The container 272 may include side lips 374. The side lips 374 of the container 272 may rest on a frame 328. The container 272 may be aligned with the rasp 205 and the trimming member 204 such that when the apparatus 200 is in use, the container 272 may receive the portions of the material 102 to be milled that pass through the apertures 212 in the base surface (not shown). In the present embodiment, the collector assembly 270 may be connected to a dispenser 280. The dispenser 280 may fill with material 102 that enters the container 272.

The container 272 may also include a gate 276. The gate 276 may be used to prevent the milled material 102 from entering the dispenser 280. For example, the gate 276 may be used to prevent any additional material 102 from entering the dispenser 280 after the dispenser has been filled. In another example, the gate 276 may be used to allow the container 272 to fill with material 102 to a certain point before removing the gate 276.

Figure 8:
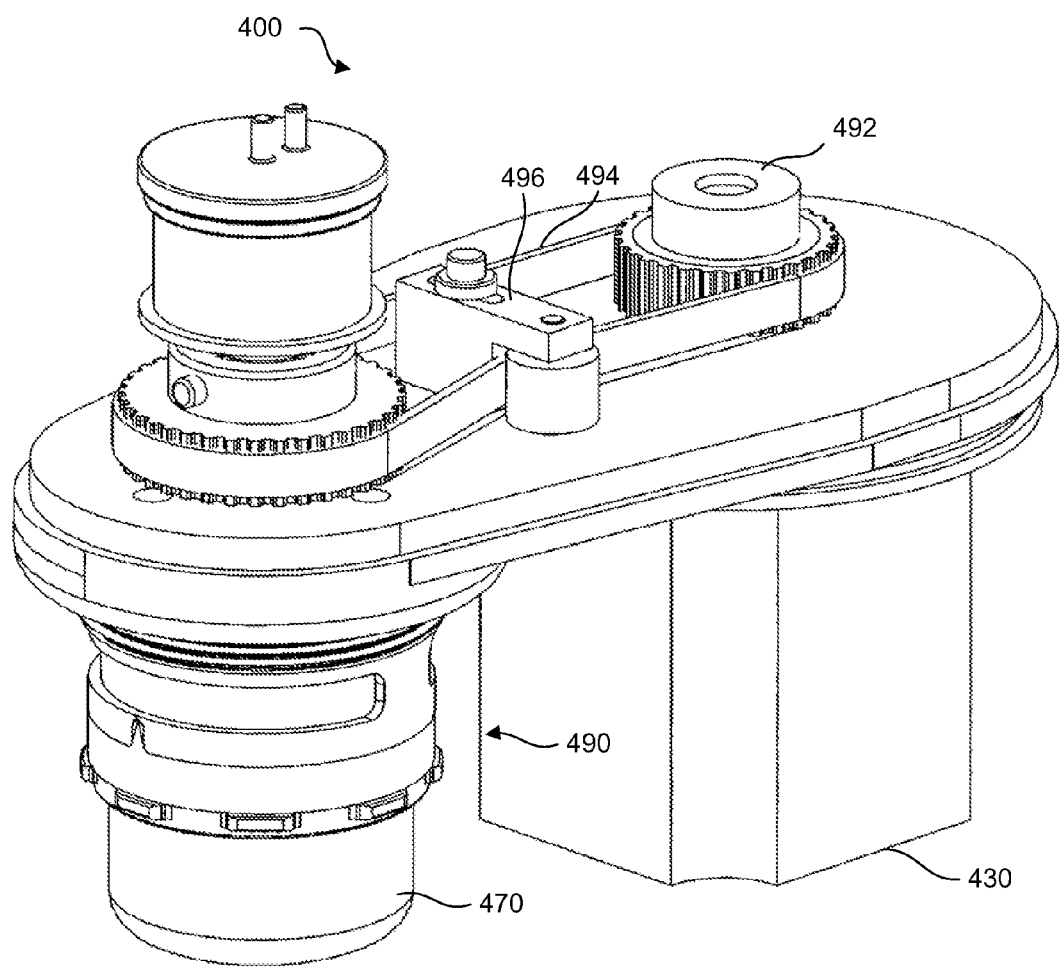
FIG. 8 is a perspective view of a partially assembled radial embodiment of an apparatus for milling material.

FIG. 8 is a perspective view of a partially assembled radial embodiment of an apparatus 400 for milling material 102. The apparatus 400 may include a motor 430 and a milling portion 490. The milling portion 490 may include a base surface (not shown), a trimming member (not shown), and a liner (not shown). The milling portion 490 may be connected to a collector assembly 470. The milling portion 490 may include a spindle (not shown). The motor 430 may drive a pulley 492. The pulley 492 may be connected to a belt 494 that may rotate the spindle. A belt tensioner 496 may be connected to the apparatus 400. The belt tensioner 496 may be used to maintain a desired tension in the belt 494.

Figure 9:
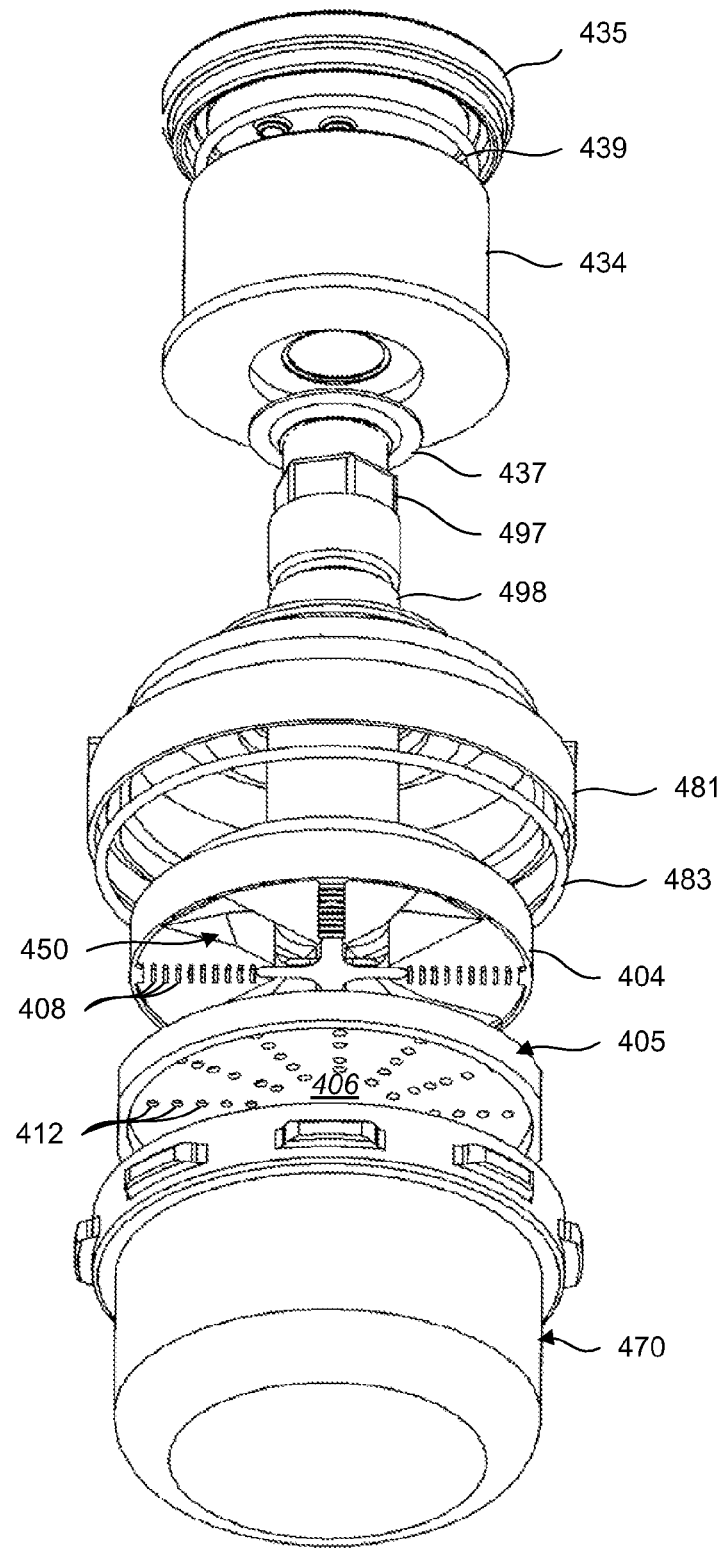
FIG. 9 is an exploded perspective view of another radial embodiment of an apparatus for milling material illustrating a collector assembly.

FIG. 9 is an exploded perspective view of another radial embodiment of an apparatus 400 for milling material 102 illustrating a collector assembly 470. The apparatus 400 may include a cover 435, a first sealing member 439 (for example, an O-ring), a funnel 434, a seal 437, a liner 481, a second sealing member 483, a coupling 497, and a spindle 498. These elements may be used to create an inner volume that is sealed, which may facilitate milling the material 102 in an airtight, sealed environment. For example, the liner 481, the second sealing member 483, and the collector assembly 470 may be connected to facilitate sealing this inner volume.

The trimming member 404 may include ramped openings 450 (similar to the openings 250 shown in conjunction with FIG. 3) between the ribs 408 that may allow the material 102 to interface with the rasp 405. The collector assembly 470 may be aligned with the rasp 405 and the trimming member 404 such that when the apparatus 400 is in use, the collector assembly 470 may receive the portions of the milled material 102 that pass through the apertures 412 in the base surface 406.

Figure 10:
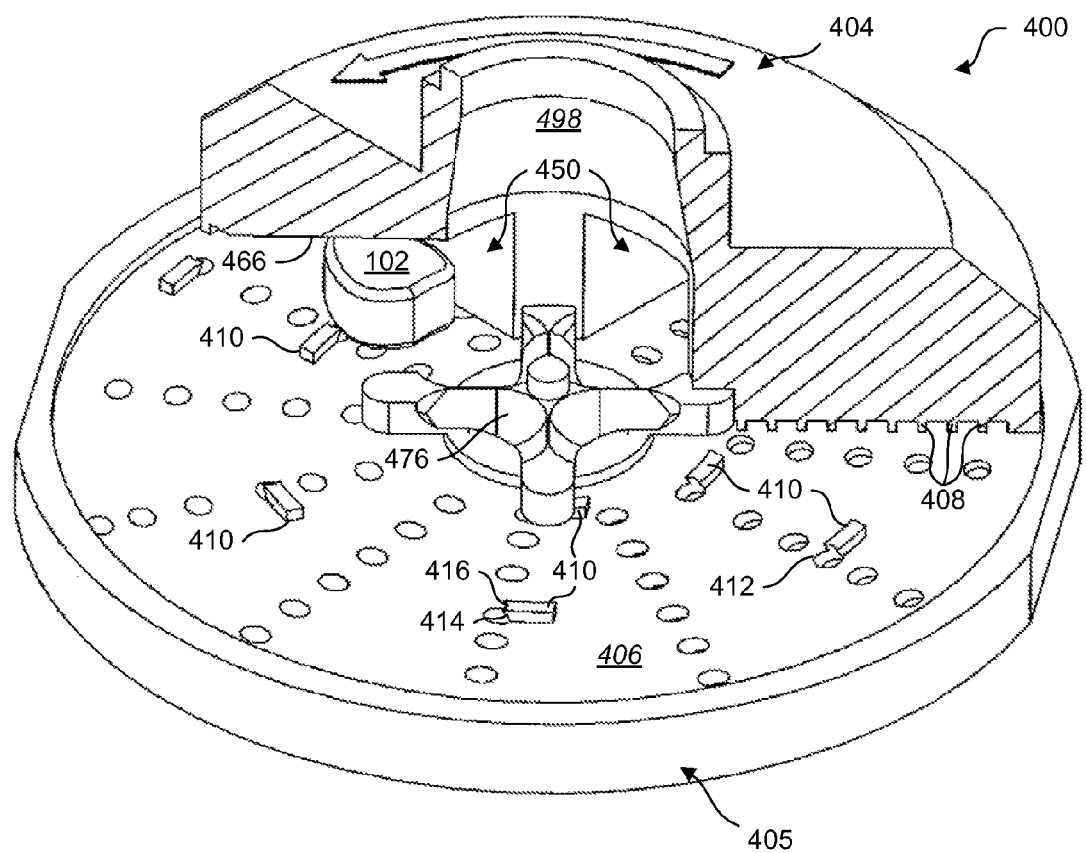
FIG. 10 is a perspective sectional view of the radial embodiment of the apparatus for milling material shown in FIG. 8.
Figure 11:
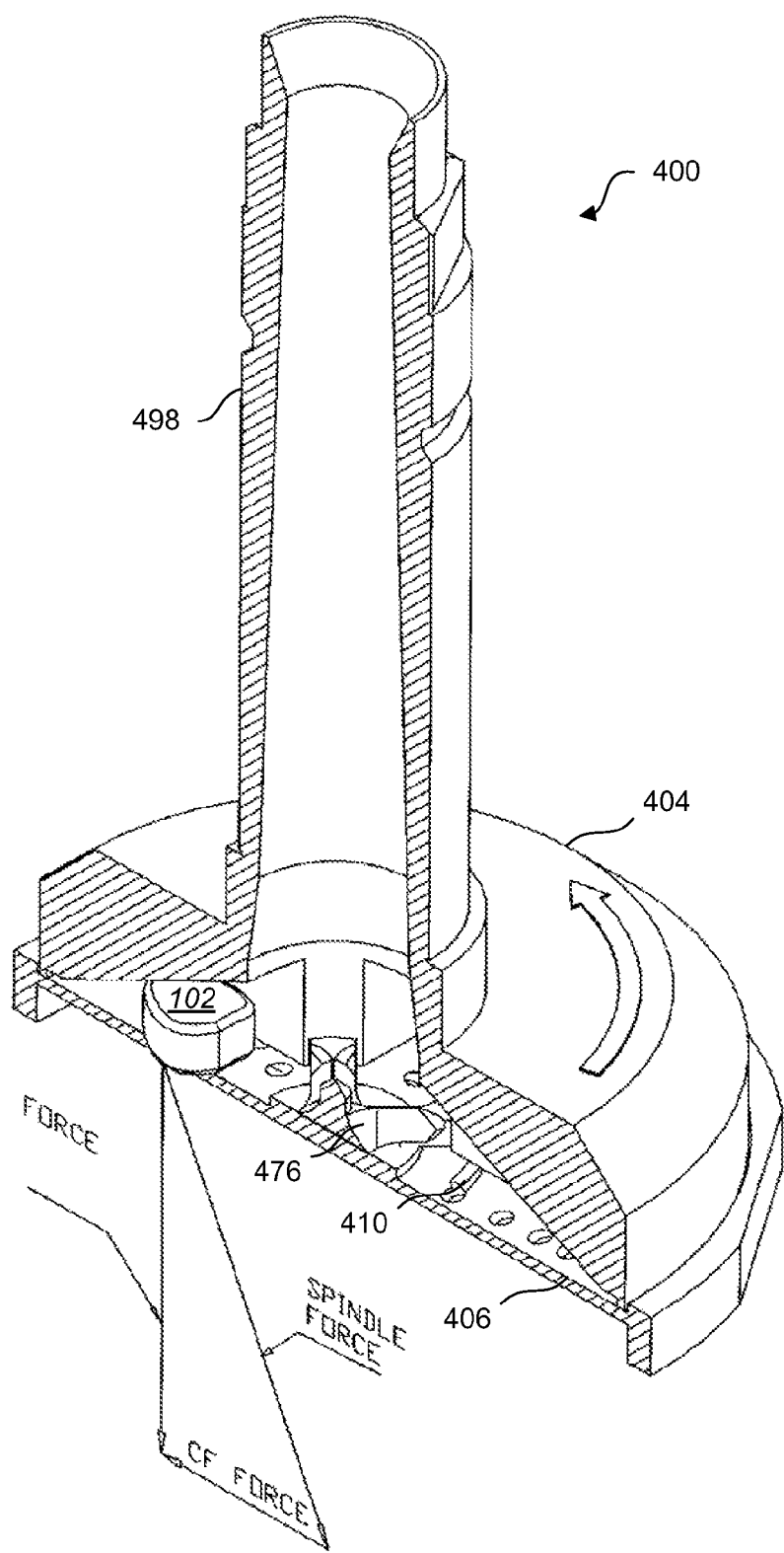
FIG. 11 is a perspective sectional view of the radial embodiment of the apparatus for milling material shown in FIG. 8.
Figure 12:
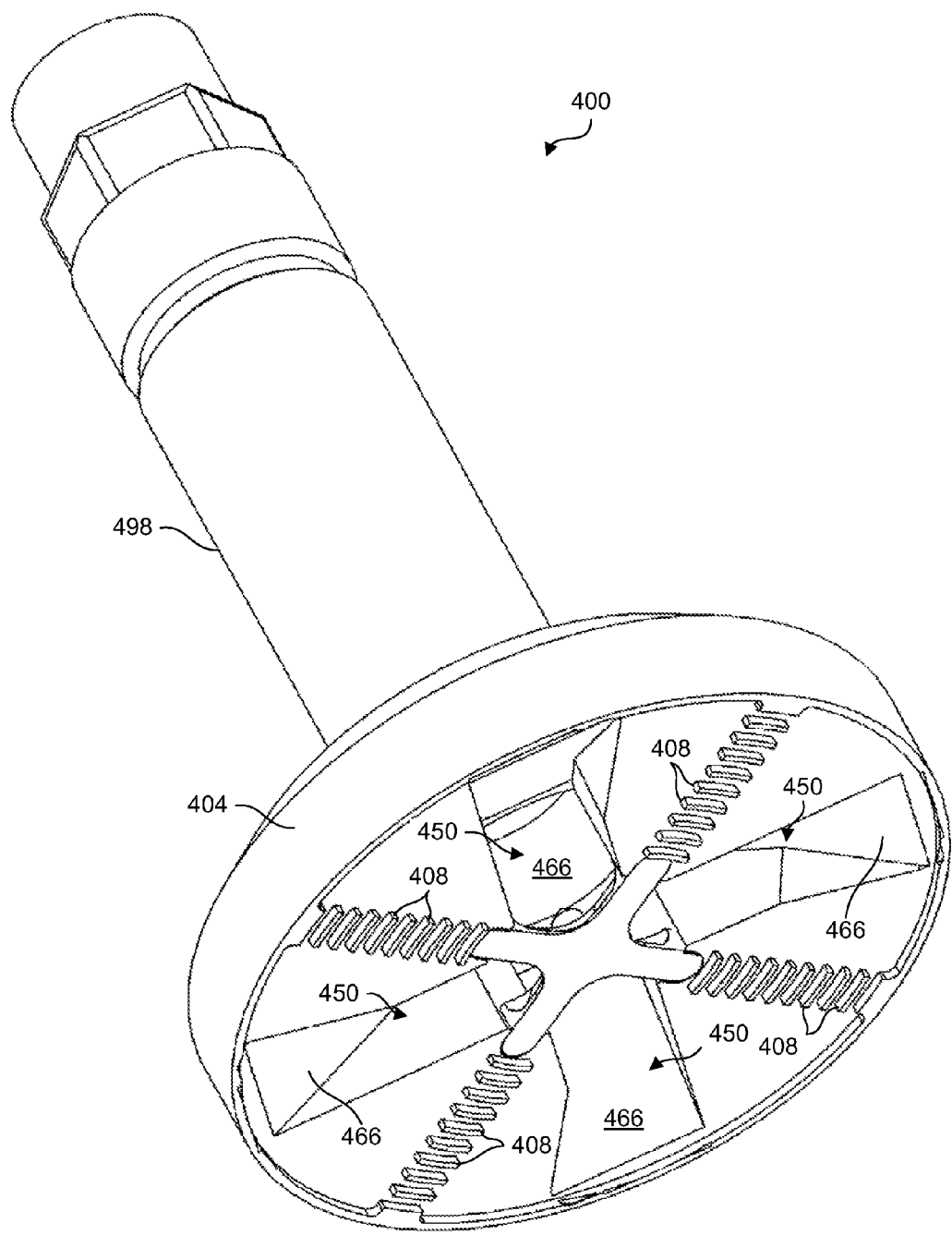
FIG. 12 is a perspective view of a spindle and trimming member of the radial embodiment of the apparatus for milling material shown in FIG. 8.

FIGS. 10, 11, and 12 are perspective sectional views of the radial embodiment of an apparatus 400 for milling material 102 shown in FIG. 8. The apparatus 400 may include a rasp 405 and a trimming member 404.

As shown in FIG. 10, the base surface 406, like the embodiment of FIG. 3, may include multiple cutting teeth 410. The cutting teeth 410, in the present embodiment, may be radially offset from each other. For example, the cutting teeth 410 may be offset from each other along a radius of the base surface 406. The cutting teeth 410 may be circumferentially offset from each other. For example, the cutting teeth 410 may be offset from each other along a circumference of the base surface 406.

In the present embodiment, some of the cutting teeth 410 are not radially offset from each other and some of the cutting teeth 410 are not circumferentially offset from each other. The trimming member 404 may include multiple ribs 408 that may interface with the various cutting teeth 410.

As shown in detail in FIG. 10, the trimming member 404 may include a ramped opening 450. The ramped openings 450 may include push surfaces 466. The ramped opening 450 and push surface 466 may cooperate to push the material 102 to be milled against the base surface 406 of the rasp 405. The ramped opening 450 may generally enclose the material 102 to be milled. In the present embodiment, the ramped opening 450 may cut through a central portion of the trimming member 404. The ramped openings 450 may include channels circumferentially between sets of ribs 408. The channels may allow the material 102 to abut the trimming member 404 and/or the push surface 466.

The base surface 406 in the present embodiment, like the base surface 206 in the embodiment of FIG. 3, may include multiple apertures 412. In the present embodiment, only one aperture 412 may be disposed adjacent a cutting tooth 410 because, in the present radial embodiment, the base surface 406 and the trimming member 404 generally may move reciprocally to facilitate disorienting and radially moving the material in the wedge channel. In other embodiments, more than one aperture 412 may be disposed adjacent each cutting tooth 410 (to further increase the milling efficiency). For example, in embodiments where the base surface 406 and the trimming member 404 move reciprocally, the cutting teeth 410 may include multiple inclined faces 414, cutting edges 416, and/or apertures 412. The base surface 406 may also include other apertures 412 that may not necessarily be disposed adjacent a cutting tooth 410.

The size of the various apertures 412 and/or cutting teeth 410 as well as the angle of the inclined faces 414 may be selected to achieve a pre-determined varied particle size distribution profile. For example, some cutting teeth 410 may be different sizes than other cutting teeth 410, some cutting teeth 410 may include inclined faces 414 of different shapes than other inclined faces 414, some apertures 412 may be different sizes than other apertures 412, and/or some apertures 412 may be of different shapes than other apertures 412. The ribs 408 may also have varied sizes.

The cutting tooth 410 may remove portions of the material 102. The removed portions of the material 102 may be of varying sizes. For example, portions of the material 102 may be removed that are approximately the size of the aperture 412, smaller than the size of the aperture 412, and/or larger than the size of the aperture 412. When a removed portion of the material 102 is larger than the size of the aperture 412, a cutting tooth 410, i.e. the same or a different cutting tooth 410, may push the removed portion of the material 102 into the trimming member 404 and remove another portion of the material 102. This process may be repeated until all of the material 102 to be milled has been directed through the aperture 412. Thus, the material 102 may be cut to generally match a predetermined varied particle size distribution profile.

The spindle 498 in the present embodiment is hollow. A hollow spindle 498 may work in conjunction with the funnel 434 to act as a hopper assembly 260 (shown in FIG. 5) to enclose the material 102 to be milled. The apparatus 400 may include a spider construct 476. The spider construct 476 may act as a cross-feeder. For example, as the material is fed through the hollow spindle 498, the spider construct 476 may direct the material 102 arriving at the opening 450 of the spindle 498 away from the center such that the material 102 may experience the radial centrifugal forces as the spindle 498 rotates.

The present embodiment is a radial embodiment of an apparatus 400 for milling material 102, because the base surface 406 and the trimming member 404 may move radially relative to each other. For example, the base surface 406 or the trimming member 404 may be rotated via a spindle 498. In another example, the base surface 406 or the trimming member 404 may be rotated via two separate spindles (not shown).

In the present embodiment, the base surface 406 does not move reciprocally (i.e. alternately clockwise and counter-clockwise). In other embodiments, the base surface 406 may move reciprocally in a radial direction relative to the trimming member 404. In embodiments where the base surface 406 may include a cutting tooth 410 with more than one cutting edge 416 and inclined face 414, this reciprocal motion may allow the cutting tooth 410 to remove portions of the material 102 to be milled on both a clockwise and a counter-clockwise rotation of the base surface 406. For example, if the base surface 406 moves reciprocally, a cutting tooth 410 may remove portions of the material 102 to be milled as the base surface 406 and/or the trimming member 404 rotates clockwise and the cutting tooth 410 may remove portions of the material 102 to be milled as the base surface 406 and/or the trimming member 404 rotates counterclockwise.

The apparatus 400 may include a push surface 466. The push surface 466 may be inclined with respect to the base surface 406 and may be used to direct the material 102 to be milled such that the material 102 may be pressed against the base surface 406. The push surface 466 may prevent material 102 from merely being chipped by a cutting tooth 410 by generally restraining the vertical motion of the material. However, as shown in detail in FIG. 10 and in contrast to the push rod 264 in the embodiment of FIG. 4, the push surface 466 may not apply pressure in response to a direct force on the push surface 466 toward the material 102 to be milled. Rather, the centrifugal forces that may be applied to the material 102 to be milled may direct the material 102 toward the push surface 466 such that the centrifugal forces push against the push surface 466. As shown in FIG. 11, the push surface 466 may generate a force to push the material 102 toward the base surface 406 such that as the cutting tooth 410 pushes the piece of material 102 against the trimming member 404 so that the cutting tooth 410 may remove a portion of the material 102.

Figure 13:
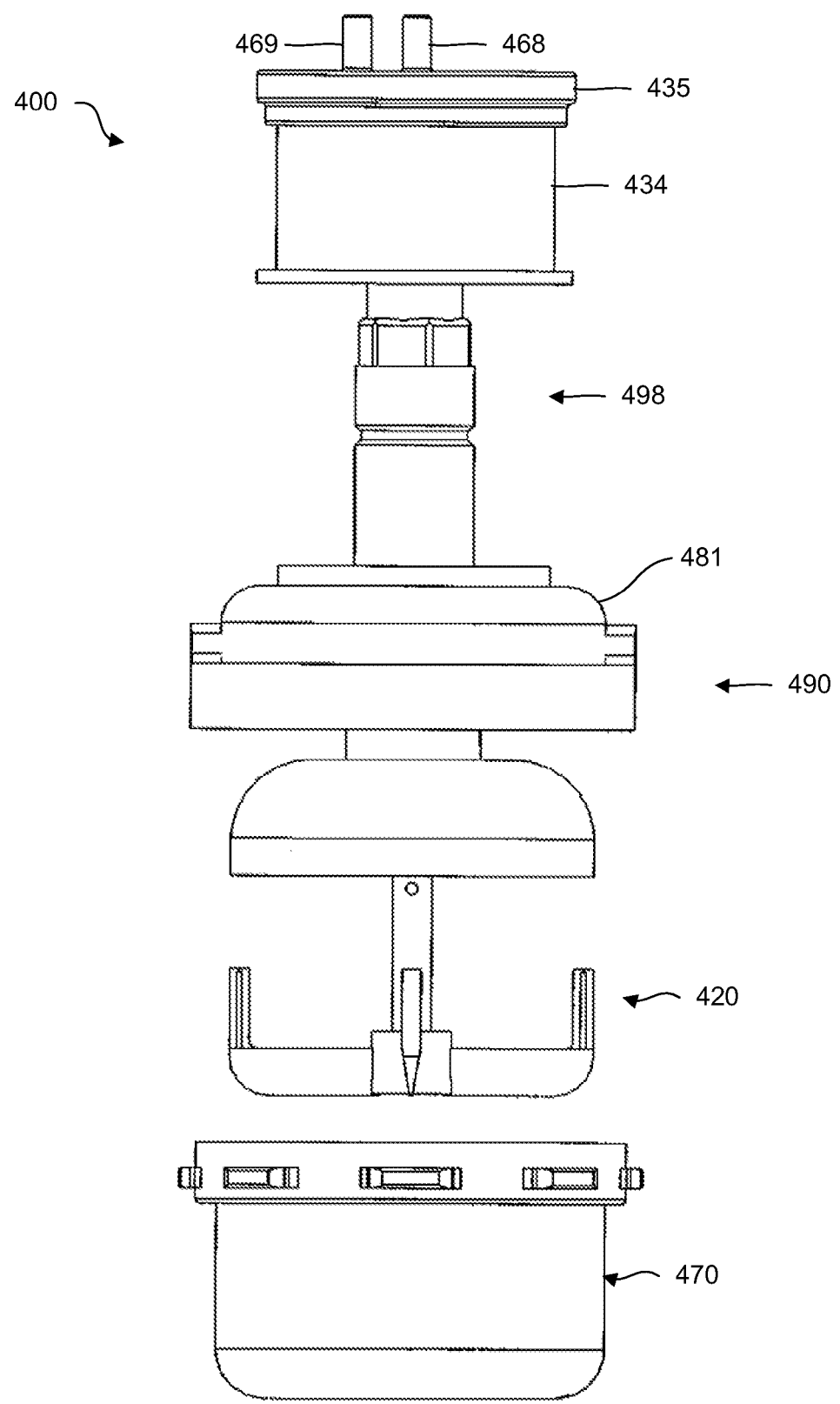
FIG. 13 is an exploded perspective view of another radial embodiment of an apparatus for milling material illustrating a mixing paddle, a collector assembly, and a milling portion.

FIG. 13 is a partially exploded front view of the radial embodiment of an apparatus 400 for milling material 102 illustrating a mixing paddle 420, a collector assembly 470, and a milling portion 490. The milling portion 490 may include a rasp (not shown), a trimming member (not shown), and a liner 481. The apparatus 400 may include a mixing paddle 420. The mixing paddle 420 may be connected to the spindle 498 such that as the spindle 498 rotates, the mixing paddle 420 may also rotate. In the present embodiment, the mixing paddle 420 may be separately connected to the spindle 498 after the rasp 405 (shown in FIG. 10) is removed. The collector assembly 470 may be removed to allow the rasp 405 and/or the trimming member 404 (shown in FIG. 10) to be removed from the spindle 498. The mixing paddle 420 may then be connected to the spindle 498 and the collector assembly 470 reconnected to the apparatus 400.

The apparatus 400 may include a funnel 434, a cover 435, and a spindle 498. These elements may be used to create an inner volume that is sealed, which may facilitate milling the material 102 in an airtight, sealed environment. The apparatus 400 may also include a fluid port 468 and a vacuum port 469. The fluid port 468 may be used to add fluids to the milled material 102. The fluids and milled material 102 may be mixed in the collector assembly 470 by the mixing paddle 420 to make a paste. Because the apparatus 400 may include a sealed inner volume, the vacuum port 469 may be used to create a vacuum within the sealed inner volume. Mixing under vacuum may facilitate replacing the air pockets in and around the milled material 102 with the added fluids. Moreover, mixing under vacuum may prevent aerating the paste during mixing.

In other embodiments, the mixing paddle 420 may be connected to the spindle 498 and located below the base surface (not shown). The mixing paddle 420 may be contained within the collector assembly 470. Thus, as the milled material 102 passes through the base surface (not shown) and is collected in the collector assembly 470, the mixing paddle 420 may mix the material 102. Other connections between the mixing paddle 420 and the spindle 498 are contemplated. For example, the mixing paddle 420 may be connected indirectly to the spindle 498 by a connection to the trimming member (not shown), the rasp (not shown), and/or other connections.

Various components of the disclosed apparatuses 200, 300, 400 may be disposable. For example, the rasps 205, 405, liner 481, and/or collection assembly 270, 470 may be removed and discarded after use. Other components of the disclosed apparatuses 200, 300, 400 may be autoclaved and reused.

The foregoing descriptions illustrate general principles that may be applied to mill material. The following is an example of a potential method for using these principles. Material 102 to be milled may be enclosed prior to being milled. For example, a hopper assembly 260 or a funnel 434 and hollow spindle 498 may enclose the material 102 to be milled.

A push surface, i.e. the push surface 266 of the push rod 264 (shown in FIG. 5) or the push surface 466 of the ramped openings 450 (shown in FIG. 10), may direct the material 102 to be milled toward the base surface 106 of the rasp 105. A cutting tooth 110 may engage a piece of the material 102 to be milled and may remove a piece of the material 102. The material 102 may be removed when the material 102 abuts the ribs 108 of the trimming member 104 and the cutting tooth 110. The milled material 102 may pass through the base surface 106 of the rasp 105 into a collector assembly 270, 470.

The milled material 102 may be mixed with other ingredients to form a paste. In some embodiments, the milled material 102 is mixed with other ingredients under a vacuum to prevent air pockets from entering the paste. The paste may be dispensed using a dispenser 280. Forming a paste with the freshly milled material 102 may provide an improved paste.

For example, making a paste of a material 102 freshly milled from a bone may create a more effective paste for bone grafts.

The apparatuses 200, 300, 400 and methods disclosed may be particularly suitable for culling live bone chips, cutting the chips into a desired particle size distribution profile, making a paste of the cut chips, and/or applying the paste for use with a bone graft. The methods and apparatuses 200, 300, 400 may also be used in other applications where a desired particle size distribution profile may be desired.

The methods disclosed herein comprise one or more steps or actions for achieving the described method. The method steps and/or actions may be interchanged with one another without departing from the scope of the present invention. In other words, unless a specific order of steps or actions is required for proper operation of the embodiment, the order and/or use of specific steps and/or actions may be modified without departing from the scope of the present invention.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

What is claimed is:

1. An apparatus for milling material to a predetermined particle size distribution profile, comprising:
    a base surface comprising:
        a first cutting tooth raised from a surrounding surface for cutting the material; and
        a first aperture in the surrounding surface of a predetermined size disposed adjacent the first cutting tooth so that material of less than the predetermined size may pass through the first aperture;
    a trimming member comprising:
        a first and a second rib for interfacing with the first cutting tooth to effect trimming of the material; and
    a chute for receiving the material,
    wherein the base surface and the trimming member are operable to move longitudinally relative to each other, to move laterally relative to the chute, and to interface to trim and cut material when placed on the base surface during the relative movement of the base surface and the trimming member.

2. The apparatus of claim 1, wherein the base surface further comprises a second cutting tooth and a second aperture disposed adjacent to the second cutting tooth, wherein the trimming member further comprises a third rib that interfaces with the second cutting tooth to effect the cutting and trimming of the material.

3. The apparatus of claim 2, wherein the first cutting tooth and the second cutting tooth are different sizes such that the material is milled to fit a predetermined particle size distribution profile.

4. The apparatus of claim 2, wherein the first cutting tooth and the second cutting tooth are laterally offset from each other so that at least one of the ribs may be positioned between the cutting teeth during the relative movement of the base surface and the trimming member.

5. The apparatus of claim 3, wherein the first cutting tooth and the second cutting tooth are offset from each other in one or more of the following directions: circumferentially, laterally, or longitudinally.

6. The apparatus of claim 1, wherein the first cutting tooth further comprises a first inclined face.

7. The apparatus of claim 6, wherein the first aperture is disposed adjacent the first inclined face and wherein an angle between the first inclined face and the base surface is less than about ninety degrees.

8. The apparatus of claim 6, wherein the first aperture is arcuately aligned with the first inclined face.

9. The apparatus of claim 1, wherein the base surface further comprises a second aperture of a predetermined size so that material of less than the predetermined size may pass through the second aperture.

10. The apparatus of claim 9, wherein the first cutting tooth further comprises a second inclined face, wherein a third aperture is disposed adjacent the second inclined face, and wherein the third aperture is of a predetermined size so that material of less than the predetermined size may pass through the third aperture.

11. The apparatus of claim 10, wherein at least one of the first aperture, the second aperture, and the third aperture are different sizes such that the material is milled to fit a predetermined particle size distribution profile.

12. The apparatus of claim 1, further comprising a push surface disposed to direct the material toward the base surface and to restrict movement of the material on the base surface.

13. The apparatus of claim 1, further comprising a container for collecting material passing through the apertures during milling.

14. The apparatus of claim 1, further comprising a drive mechanism for moving the base surface and trimming member relative to each other.

15. An apparatus for milling material to within a predetermined particle size distribution profile, comprising:
    a base surface comprising:
        a first cutting tooth raised from a surrounding surface for cutting the material, the first cutting tooth having an inclined face; and
        a first aperture in the surrounding surface of a predetermined size disposed adjacent the first cutting tooth so that material of less than the predetermined size may pass through the first aperture;
    a trimming member comprising:
        a first rib and second for interfacing with the first cutting tooth to effect trimming of the material; and
    a chute for receiving the material,
    wherein the base surface and the trimming member are operable to move longitudinally relative to each other and to move laterally relative to the chute, wherein the inclined face of the first cutting tooth and first and second ribs interface to trim and cut material when placed on the base surface during the relative movement of the base surface and the trimming member.

16. The apparatus of claim 15, wherein the base surface further comprises a second cutting tooth and wherein the trimming member further comprises a third rib that interfaces with the second cutting tooth to effect the cutting and trimming of the material.

17. The apparatus of claim 16, wherein the first cutting tooth and the second cutting tooth are laterally offset from each other so that at least one of the ribs may be positioned between the cutting teeth during the relative movement of the base surface and the trimming member.

18. The apparatus of claim 17, wherein the first cutting tooth and the second cutting tooth are laterally and/or longitudinally offset from each other.

19. The apparatus of claim 15, further comprising a push surface disposed to direct the material toward the base surface and to restrict vertical, longitudinal, and lateral movement of the material on the base surface, and wherein the base surface and trimming member move longitudinally relative to each other and laterally relative to the push surface.

20. The apparatus of claim 19, wherein the push surface is connected to a push rod disposed to direct the material toward the base surface and to restrict movement of the material on the base surface.

21. The apparatus of claim 15, further comprising at least one drive mechanism for moving the base surface and trimming member relative to each other and a push surface.

22. The apparatus of claim 15, further comprising a container for collecting material passing through the aperture during milling.

23. The apparatus of claim 22, wherein the container for collecting material passing through the apertures during milling may be used to dispense the material.

24. An apparatus for milling material to within a predetermined particle size distribution profile, comprising:
   a base surface comprising:
      a first cutting tooth for cutting the material; and
      a first aperture of a predetermined size disposed adjacent the first cutting tooth so that material of less than the predetermined size may pass through the first aperture;
   a trimming member comprising:
      a first and a second rib for interfacing with the first cutting tooth to effect trimming of the material; and
   a push surface inclined with respect to the base surface and disposed to direct the material toward the base surface as the material is moved by centrifugal force in a radial direction during relative radial movement of the base surface and the trimming member;
   wherein the base surface and the trimming member are operable to move radially relative to each other and to interface to trim and cut material when placed on the base surface during the relative movement of the base surface and the trimmer member.

25. The apparatus of claim 24, wherein the base surface further comprises a second cutting tooth and a second disposed adjacent to the second cutting tooth, wherein the trimming member further comprises a third rib that interfaces with the second cutting tooth to effect the cutting and trimming of the material during the relative movement of the base surface and the trimmer member.

26. The apparatus of claim 25, wherein the first cutting tooth and the second cutting tooth are radially offset from each other so that at least one of the fibs may be positioned between the cutting teeth during the relative movement of the base surface and the trimming member.

27. The apparatus of claim 26, wherein the first cutting tooth and the second cutting tooth are radially and/or circumferentially offset from each other.

28. The apparatus of claim 24, further comprising a spider construct that encourages the material away from the axis of rotation during the relative movement of the base surface and the trimmer member so that centrifugal force will act upon the material as the apparatus is rotated.

29. The apparatus of claim 24, further comprising:
   a rotatable mixer paddle that is connected to the trimming member such that the rotatable mixer paddle moves relative to the base surface.

30. The apparatus of claim 29, further comprising a drive mechanism for moving the base surface and trimming member relative to each other and for rotating the mixer paddle to mix the material.

31. The apparatus of claim 29, further comprising a container for collecting material passing through the apertures during milling.

* * * * *